United States Patent [19]

Lindemann

[11] Patent Number: 4,598,703
[45] Date of Patent: Jul. 8, 1986

[54] HEMI-ARM SLING

[75] Inventor: Peer Lindemann, West Bend, Wis.

[73] Assignee: Rolyan Manufacturing Co. Inc., Menomonee Falls, Wis.

[21] Appl. No.: 783,164

[22] Filed: Oct. 2, 1985

[51] Int. Cl.[4] .............................................. A61F 5/00
[52] U.S. Cl. ........................................ 128/94; 128/77
[58] Field of Search ................... 128/94, 133, 134, 77, 128/78

[56] References Cited

U.S. PATENT DOCUMENTS 2,310,566  2/1943  Anderson ........................ 128/94 X
4,476,859  10/1984  Kloepfer et al. .................. 128/94 X

FOREIGN PATENT DOCUMENTS 479873  5/1916  France ................................. 128/77

OTHER PUBLICATIONS

Athletic Injuries, etc; Thorndike; Orthopedic Support Atlas; Feborger; 1942; pp. 87–88.

Primary Examiner—Sheldon J. Richter
Attorney, Agent, or Firm—Ira Milton Jones

[57] ABSTRACT

A hemi-arm sling for treatment to a shoulder subluxation and injuries involving the ligaments and tendons. The sling is adjustable to position the head of the humerus in the glenoid-fossa without restricting circulation of a flaccid arm.

20 Claims, 4 Drawing Figures

U.S. Patent Jul. 8, 1986 Sheet 1 of 2 4,598,703
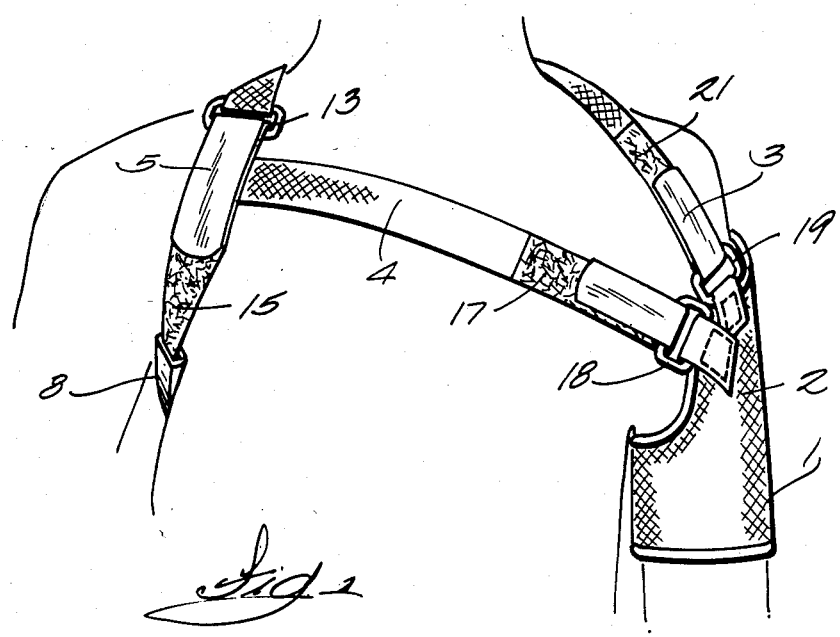
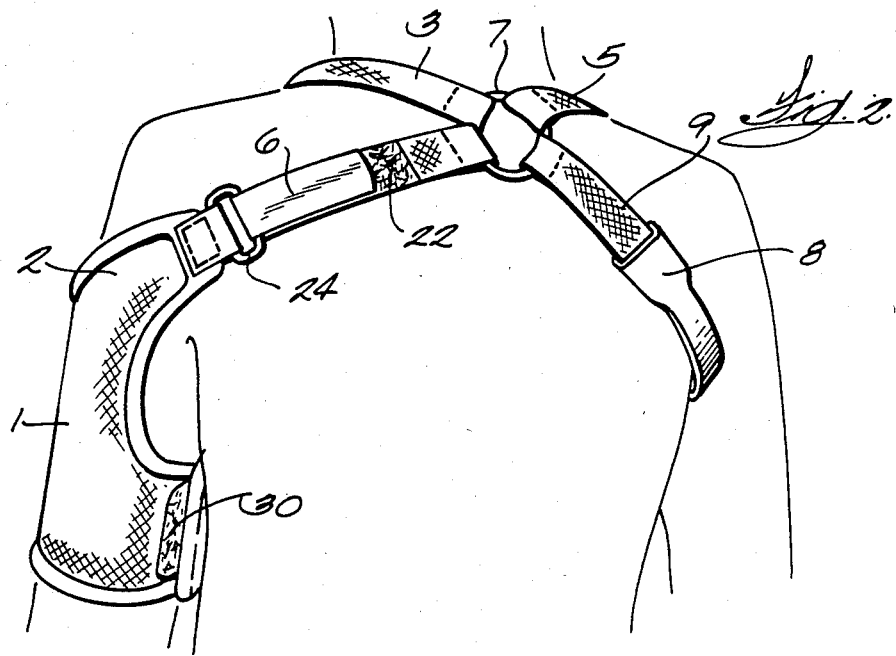

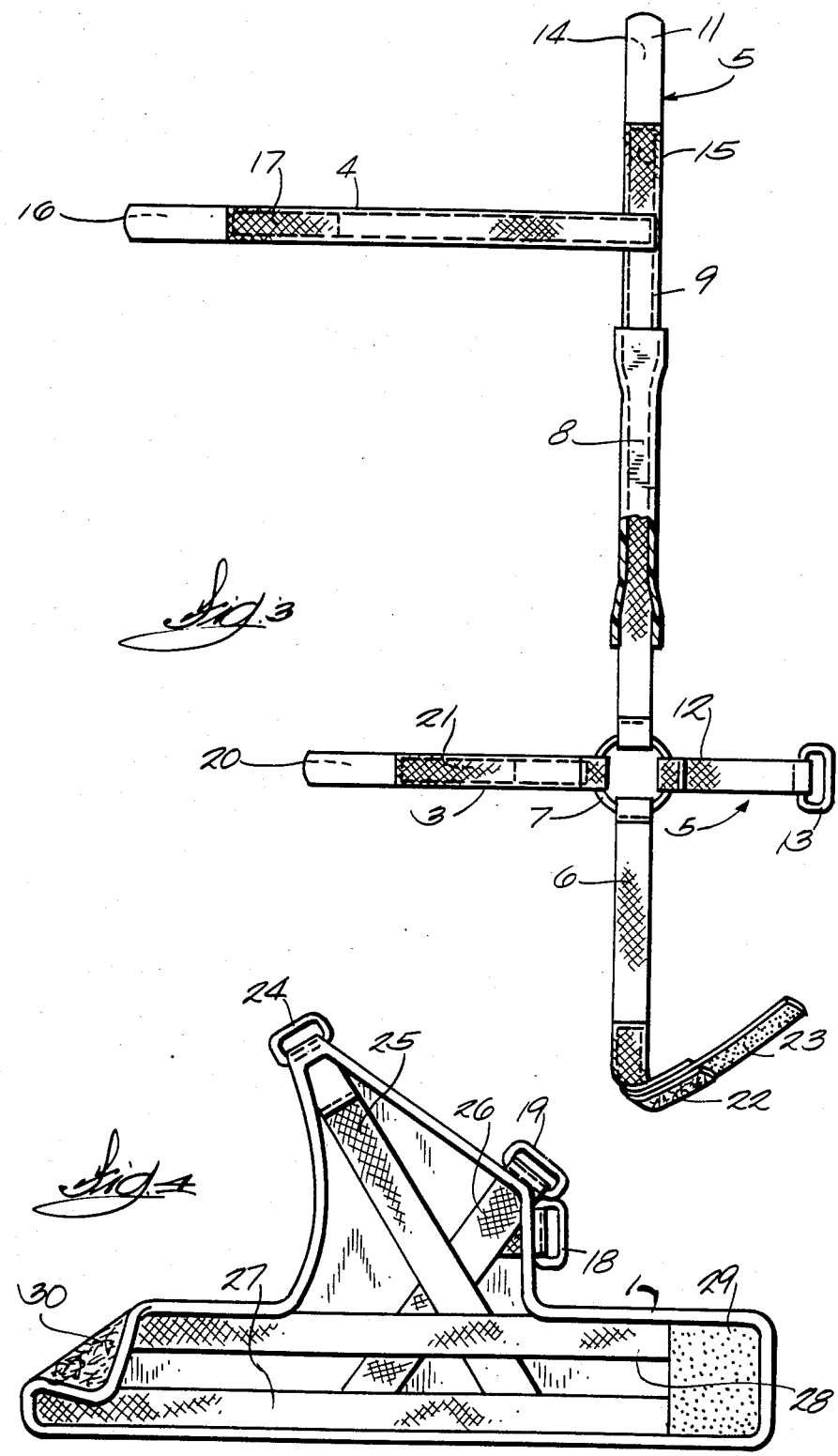

HEMI-ARM SLING

This invention relates to an arm sling, and more particularly to a hemi-arm sling having adjustable means to position a humerus by lifting or lowering, and rotation for comfort and convenience of the patient.

The recovery of a patient following cerebro-vascular accident is affected by the extent of the brain damage and the development of complications. Development of a painful shoulder in the hemiplegic patient is a significant and serious problem because it can limit the patient's ability to reach his or her maximum functional potential. Shoulder pains have been identified, such as immobilization of the upper extremity, trauma of the joint structure, including brachial plexus injuries and subluxation of the gleno-humeral joint; or it may be a combination of these symptoms.

For treatment of the patient effectively the basic anatomy and kinesiology of the shoulder complex should be understood. A sling can be very helpful in treating the patient. The sling should control the position of the humeral head in the glenoid-fossa and provide proper support and rotation of the humerus for the comfort of the patient.

Accordingly, applicant has provided a hemi-arm sling for carrying the humerus and adjustably lifting and lowering the humerus and to rotate and counter-rotate it to provide the proper position of the gleno-humeral joint.

It is an object of this invention to provide a hemi-arm sling for positioning of the humerus in the gleno-humeral joint without restricting circulation.

It is another object of this invention to provide a hemi-arm sling for supporting the humerus and having anterior and posterior straps to control the internal and external rotation of the humerus.

It is a further object of this invention to provide a hemi-arm sling having a humeral cuff and a clavical strap to lift and lower the humerus and anterior and posterior straps to control the internal and external rotation.

The objects of this invention are accomplished in a hemi-arm sling having an adjustable humeral cuff for supporting and rotating the injured arm. An axilla loop embraces the unaffected shoulder and is connected to a posterior tension distribution ring. An anterior strap extends between the axilla loop and the humeral cuff to provide internal rotational adjustment. A clavical strap and a posterior strap extend between the posterior tension distribution ring and the humeral cuff to support the cuff and also adjustably control the external rotation of the cuff.

Referring to the drawings:

FIG. 1 illustrates the hemi-arm sling positioned on a patient as viewed from the front;

FIG. 2 is a view of the hemi-arm sling on the patient, as viewed from the rear;

FIG. 3 is a view of a portion of the hemi-arm sling including the straps for supporting and adjusting the humeral cuff;

FIG. 4 illustrates the humeral cuff as viewed from a side of the cuff.

Referring to the drawings, the humeral cuff 1 is formed with a vertically extending flap 2. The flap is adapted for connection to a clavical strap 3 and the anterior strap 4. The anterior strap 4 is connected to the axilla loop 5 which embraces the unaffected shoulder of the patient. The humeral cuff 1 is adjustable to fit the arm of the patient with sufficient tightness to position the arm and avoid restricting circulation.

As viewed in FIG. 2, the flap 2 extends vertically and rearwardly for connection to the posterior strap 6 which, in turn, is connected to the tension distribution ring 7. The axilla loop 5 embraces the unaffected shoulder and both ends of the loop extend to the tension distribution ring 7 where they are attached. The axilla loop is of non-elastic material but is adjustable to suit the patient. A sheath 8 encases a portion of the axilla loop which extends under the arm.

The hemi-arm sling consists essentially of two components. These components are the harness 9, as shown in FIG. 3, and the humeral cuff 1, shown in FIG. 4. The harness includes the tension distribution ring 7 and the axilla loop 5 which comprises two straps 11 and 12. The strap 12 is provided with a D-ring 13 which is fastened to the end of the strap 11. The end of the strap 11 includes fastening means, preferably consisting of a portion of Velco hooks 14 and Velco loops 15. The loop is fastened by inserting the end 14 into the D-ring and folding the hook portion 14 against the loop portion 15 when the sling is mounted on the patient.

It is understood that the fastening means, as illustrated, as illustrative and not limiting, and that other fastening means could also be used for fastening these two parts together.

The anterior strap 4 is integral with the strap 11 of the axilla loop. The anterior strap 4 extends normally from the strap 11 and is preferably provided with a Velco hook portion 16 and Velcro loop portion 17 to provide a fastening means when it is inserted in the D-ring 18 of the humeral cuff.

The clavical strap 3 is connected to the tension distribution ring and extends over the affected shoulder of the patient for connection to the D-ring 19. The clavical strap 3 is preferably also provided with a Velcro hook portion 20 and Velco loop portion 21 to provide a fastening means for the clavical strap.

The posterior strap 6 is also provided with a fastening means, preferably consisting of Velcro loop portion 22 and Velcro hook portion 23. The Velcro fastening means is adapted for connection with the D-ring 24 in the assembled position installed on the patient. The anterior strap 4, clavical strap 3 and posterior strap 6 are preferably elastic, so that they can stretch or contract depending on the needs during its use on the patient.

The cuff shown in FIG. 4 is reinforced by the reinforcing straps 25, 26, 27 and 28. The cuff is provided with fastening means, preferably a Velcro hook portion 29 and a Velcro loop portion 30 to provide adjustment for sizing the humeral loop on the arm of the patient.

The operation of the device will be subsequently described.

To place the sling on a patient, detach the elasticized anterior strap from the D-ring on the humeral cuff. The hemi-arm sling can then be draped over the affected shoulder, folding the posterior flap of the humeral cuff around the arm and overlapping with the anterior flap. The cuff should be adjusted to fit the humeral portion of the arm but not restrict circulation. Compression of the humeral cuff around the arm should avoid free movement of the humeral cuff, but be snug enough so that it holds the arm.

Detach the end of the axilla loop and allow the loop to drape over the shoulder, then insert the end of the strap 11 of the axilla loop in the D-ring 13 and fasten the Velcro fastening means to form a loosely positioned loop on the unaffected shoulder. Bring the anterior elasticized strap across the front, looping it through the D-ring 18 of the humeral cuff and secure to the D-ring by the fastening means. The clavical strap and the posterior straps are then adjusted for the desired vertical humeral postion of the cuff. The posterior strap can then be adjusted to provide the degree of external rotation required. Once the degree of rotation is achieved, the anterior strap is adjusted to provide the internal rotation required.

The vertical position of the humeral cuff is essentially adjusted by the clavical strap which extends over the affected shoulder of the patient. Once the proper position is achieved for the straps on the harness, a marking pencil may be used for convenience in removal and repositioning of the hemi-arm sling.

The embodiments of the invention in which an exclusive property or privilege is claimed are defined as follows:

1. A hemi-arm sling comprising:
   an adjustable humeral cuff for embracing an arm;
   a posterior tension distribution ring for distributing tension;
   a posterior strap connected between said cuff and said ring to regulate the degree of external rotation of the humeral cuff;
   a clavical strap connected between said cuff and said ring extending over an affected shoulder for vertically positioning the humeral cuff;
   a shoulder loop connected to said ring and embracing the unaffected shoulder;
   an anterior strap connected between said shoulder loop and said cuff for adjusting the degree of internal rotation of said cuff to thereby provide an adjustable shoulder support.

2. A hemi-arm sling as set forth in claim 1, including an elasticized material forming said anterior strap and said posterior strap.

3. A hemi-arm sling as set forth in claim 1, including Velcro adjustable fastening means on said cuff to adjustably adjust firmness of support for the arm.

4. A hemi-arm sling comprising:
   an ajustable humeral cuff for embracing and supporting an arm of an affected shoulder;
   a supporting harness connected to said cuff for supporting said humeral cuff including an axilla loop embracing the unaffected shoulder;
   a tension distribution ring connecting said axilla loop;
   a clavical strap connected between the tension distribution ring and said humeral cuff for carrying the weight of said humeral cuff and arm of the affected shoulder;
   an anterior strap connected between said axilla loop and said humeral cuff for adjustably controlling the degree of internal rotation of the cuff;
   a posterior strap connected between a tension distribution ring and said humeral cuff for adjustably controlling the degree of external rotation of said arm and thereby provide an adjustable shoulder support.

5. A hemi-arm sling as set forth in claim 4, wherein said tension distribution ring defines a circular ring for distributing tension transmitting through said posterior strap and said clavical strap to said tension distribution ring for transmittal to said axilla loop for carrying said humeral cuff.

6. A hemi-arm sling as set forth in claim 4, including an elasticized material forming said clavical strap.

7. A hemi-arm sling as set forth in claim 4, including means adjustably adjusting the firmness of support of the arm by said humeral cuff.

8. A hemi-arm sling as set forth in claim 4, wherein said posterior strap runs diagonnally to provide partial support and partial external rotational adjustment on said humeral cuff.

9. A hemi-arm sling as set forth in claim 4, including a fabric material defining said straps.

10. A hemi-arm sling as set forth in claim 4 including increment adjusting means on said humeral cuff to adjustably adjust the tightness or looseness of the cuff on said arm.

11. A hemi-arm sling as set forth in claim 4, including reinforcing means in said cuff to carry the strain at the connections of said straps to said cuff.

12. A hemi-arm sling as set forth in claim 4, including reinforced supporting structure connecting said straps to said cuff and maintaining the shape of said humeral cuff.

13. A hemi-arm sling as set forth in claim 4, including Velcro adjustable fastening means on said straps to adjustably vary the length of said straps for comfort of the patient.

14. A hemi-arm sling as set forth in claim 4, including reinforcing means aligned with the straps to reinforce the humeral cuff for maintaining its shape and dimensions.

15. A hemi-arm sling as set forth in claim 4, wherein said straps include elastic webbing to provide comfort in use of said sling.

16. The arm sling as set forth in claim 4, wherein said tension distribution ring defines a circular ring for distributing the weight of said cuff and arm through said ring for transmission to said axilla loop for carrying the weight of said cuff and arm on said axilla loop.

17. The hemi-arm sling as set forth in claim 4, including a sheath material encasing said axilla loop to provide a softer broader bearing surface on said unaffected shoulder for carrying the weight of said cuff and arm.

18. A hemi-arm sling as set forth in claim 4, including padding on said cuff to provide a softer bearing surface for engaging the arm.

19. A hemi-arm sling comprising:
   an ajustable humeral cuff having a supporting flap for embracing an arm and supporting an arm of an affected shoulder;
   a supporting harness connected to said flap of said cuff for supporting said humeral cuff, including an axilla loop embracing the unaffected shoulder;
   a weight-distribution ring connection to said axilla loop;
   a clavical strap connected between said weight distribution ring and said flap of said cuff for carrying the weight of said humeral cuff and arm of said shoulder;
   an interior strap connected between said axialla loop and said flap on said cuff to adjustably control the degree of internal rotation;
   a posterior strap connected between said weight distribution ring and said flap on said cuff for adjustably controlling the degree of external rotation and thereby providing an adjustable shoulder support.

20. A hemi-arm sling as set forth in claim 19, including
   D-rings on the flap of said humeral cuff for connecting said straps to said humeral cuff.

* * * * *